United States Patent

Mueller

Patent Number: 5,925,793
Date of Patent: Jul. 20, 1999

[54] PREPARATION OF TERTIARY AMINES

[75] Inventor: Herbert Mueller, Frankenthal, Germany

[73] Assignee: BASF Aktiengesellschaft, Ludwigshafen, Germany

[21] Appl. No.: 08/117,316

[22] Filed: Sep. 7, 1993

[30] Foreign Application Priority Data

Sep. 12, 1992 [DE] Germany .............. 42 30 554

[51] Int. Cl.⁶ .................................................. C07C 209/37
[52] U.S. Cl. ................................................................ 564/480
[58] Field of Search .............................................. 564/480

[56] References Cited

U.S. PATENT DOCUMENTS

| | | | |
|---|---|---|---|
| 2,160,058 | 5/1939 | Covert | 260/583 |
| 3,366,687 | 1/1968 | Ellis et al. | 260/583 |
| 3,708,539 | 1/1973 | Fenton | 260/585 |
| 4,138,437 | 2/1979 | Strauss et al. | 260/583 |
| 4,234,727 | 11/1980 | Toussaint et al. | 544/178 |
| 4,310,697 | 1/1982 | Cheminal et al. | 564/479 |
| 4,851,578 | 7/1989 | Fischer et al. | 564/479 |
| 4,851,580 | 7/1989 | Mueller et al. | 564/479 |

FOREIGN PATENT DOCUMENTS 233 317  8/1987  European Pat. Off. .

OTHER PUBLICATIONS

Patent Abst. of Japan, vol. 9, No. 283, Nov. 9, 1985.
Houben–Weyl, "Methoden der Organischen Chemie", vol. IV, 1955.

*Primary Examiner*—Brian M. Burn
*Attorney, Agent, or Firm*—Keil & Weinkauf

[57] ABSTRACT

A process for the preparation of dialkylamines of the general formula I,

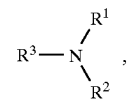
(I)

in which $R^1$, $R^2$, and $R^3$ denote $C_1$–$C_{12}$ alkyl, by the reaction of a dialkylamine of the general formula II

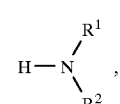
(II)

in which $R^1$ and $R^2$ denote $C_1$–$C_{12}$ alkyl, with alcohols $R^3$—OH in the presence of a (copper chromite/alkaline-earth metal chromite)-containing hydrogenation/dehydrogenation catalyst, in which the reaction is carried out in the liquid phase over a fixed bed catalyst in the presence of the water formed during the reaction at temperatures ranging from 180° to 210° C. and pressures ranging from 40 to 120 bar.

4 Claims, No Drawings

PREPARATION OF TERTIARY AMINES

The present invention relates to a process to the preparation of tertiary amines by the reaction of seconary amines with alcohols in the presence of (copper chromite/barium chromite)-containing hydrogenation/dehydrogenation catalysts at elevated temperatures and pressures.

DE-A 1,493,781 describes a process for the preparation of tertiary amines, in which at least stoichiometric amounts of a seconary amine are caused to react with an alcohol. An excess of alcohol leads to poor selectivities toward the desired tertiary amines. When primary alcohols are used, low yields and poor selectivites are achieved.

U.S. Pat No. 3,708,539 describes a process for the manufacture of tertiary amines in the liquid phase, in which process an alcohol is caused to react with a secondary amine over a catalyst based on ruthenium, osmium, rhenium, or technetium. The drawback of this process is the high cost of the catalyst raw materials.

DE-A 2,838,184 and EP-A 24,225 describe processes for the preparation of tertiary amines by the reaction of secondary amines with alcohols in the presence of copper chromite catalysts or pure copper catalysts obtainable by thermal decomposition and reduction of basic copper/aluminum carbonates, said preparation being carried out by the reaction of, say, dimethylamine with low molecular weight alcohols in the gas phase.

Although both of these processes produce, say, dimethylethylamine in a commercially satisfactory manner, the syntheses are still in need of improvement. Both processes suffer from the drawback that a relatively large amount of energy is required in order to vaporize the reactants for execution of the process in the gas phase, and it is necessary to circulate large amounts of hydrogen and gaseous dimethylamine while the product, for example dimethylethylamine, can be removed from the circulated gases only by applying high energy-consuming condensation techniques. Usually, it is necessary to employ a cascade of several condensation stages. Since these processes are carried out in the gas phase over catalysts having not only a hydrogenating but also a dehydrogenating action, the alcohol also forms the corresponding aldehyde, which undergoes aldol condensation to produce undesirable by-products, which not only reduce the yield but also appear in the end product as impurites. In the case of the synthesis of ethyidimethylamine, the crude effluent contains acetaldehyde for example. For this reason, the process described in EP-A 24,255 feeds the initially produced reaction product to a separate hydrogenation stage before it is finally worked up. In this hydrogenation stage the acetaldehyde is hydrogenated to ethanol to avoid purification problems.

EP-A 227,904 describes a process for the manufacture of tertiary amines by the reaction of secondary amines with alcohols in the liquid phase and in the presence of alkali metal oxides and/or alkaline-earth metal oxides and/or alkali metal hydroxides and/or alkaline-earth metal hydroxides and also in the presence of water and copper catalysts. The copper catalysts recommended are basic copper/aluminum carbonates produced by precipitating a copper/aluminum salt followed by thermal decomposition.

DE-A 2,535,073 also describes the alkylation of secondary amines with alcohols in the liquid phase. The catalysts used are copper chromite catalysts. The amination takes place in the liquid phase over suspended catalyst. The success of the process is governed by the necessity for constant removal of the water of reaction from the reaction mixture as it forms.

It is thus an object of the present invention to overcome the aforementioned drawbacks.

Accordingly, we have found a novel and improved process for the preparation of a trialkylamine of the general formula I

in which $R^1$, $R^2$, and $R^3$ denote $C_1$–$C_{12}$ alkyl, by the reaction of a dialkylamine of the general formula II

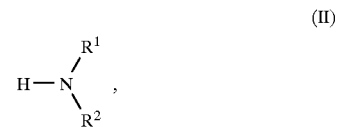

in which $R^1$ and $R^2$ denote $c_1$–$C_{12}$ alkyl, with an alcohol $R^3$—OH in the presence of a (copper chromite/alkaline-earth metal chromite)-containing hydrogenation/dehydrogenation catalyst, wherein the reaction is carried out in the liquid phase over a fixed bed catalyst in the presence of the water formed during the reaction at temperatures ranging from 180° to 210° C. and pressures ranging from 40 to 120 bar.

The process of the invention may be carried out as follows:

The secondary amine II can be caused to react with an alcohol $R^3$—OH at temperatures ranging from 160° to 250° C., preferably from 170° to 210° C. generally under superatmospheric pressure, for example, under an overall pressure of from 40 to 120 bar and preferably from 50 to 100 bar and more preferably from 60 to 100 bar and a hydrogen partial pressure of from 10 to 50 bar and preferably from 15 to 40 bar and more preferably from 20 to 35 bar. The overall pressure of the reaction is a combination of the vapor pressure of the reactants and the hydrogen partial pressure. The removal of off-gas is usually largely unnecessary, since foreign inert gases are virtually not formed in the process of the invention. At the furnace outlet the reaction product can be continuously withdrawn into a receiver, which may be operated with constant-level control. The reaction is slightly exothermal (ca 7 kcal/mol), for which reason it is easy to keep the reaction vessel isothermal by recycling a cooled portion of the reaction product to the layer of catalyst by means of a circulating pump. The effluent may contain unconverted secondary amine II and unconverted alcohol. Both can be separated by distillation and recycled to the reaction of the invention.

The molar ratio of secondary amine II to the alcohol is usually from 0.05:1 to 50:1 and is preferably from 0.5:1 to 10:1 and more preferably from 1:1 to 3:1.

The process can be carried out over fixed bed catalysts using a packed column method.

Using fixed bed catalysts the process is advantageously carried out in the following manner:

The reactor used is, eg, a vertical cylindrical vessel equipped with the usual means for cooling and heating and means for feeding the reactants. The reaction vessel can be filled with catalyst of arbitrary shape. Frequently the catalyst is used as extrudates having a diameter of from 3 to 6 mm and a length of up to 5 cm. It can be in the form of pellets or alternatively in the form of cylinders measuring, eg, 5 mm in diameter and 5 mm in height or as balls, or used in any other arbitrary form.

In the preferred embodiment of the process of the invention (copper chromite/barium chromite) catalysts are used whose barium content should be >1 wt %, in particular >3 wt %.

A catalyst which is highly suitable for amination is catalyst G22 (Südchemi), which contains in addition to oxygen 33 wt % of copper, 27 wt % of chromium, and 11 wt % of barium. If the barium in the catalysts is replaced by, for example, magnesium or calcium, these only exhibit ca 60% of the activity and ca 90% of the selectivity of the barium-containing catalysts. The preparation of the catalysts is described in the handbook Houben- Weyl, Methoden der organischen Chemie, 4th Edition, 1955, Georg Thieme Verlag Stuttgart Vol. 4/1, pp. 180 to 183. The catalysts can contain calcium chromite or magnesium chromite instead of barium chromite.

The aforementioned catalyst G22 may be used in pellet form (3×3 and 4.5×4.5 mm). The catalyst is advantageously activated prior to use by reduction with hydrogen at temperatures between 160° and 220° C.

Although the use of a catalyst having a high barium content suffices to provide adequate selectivity, it is a desirable measure in the present process to add to the reactants an alkali metal oxide, an alkaline-earth metal oxide, an alkali metal hydroxide, and/or an alkaline-earth metal hydroxide. This measure makes it possible to suppress transalkylation reactions and disproportionation in a particularly advantageous manner. And it is surprising to observe that this effect occurs to an increasing extent if the alkali metal or alkaline-earth metal compound is continuously fed to the liquid reactants. This effect is less pronounced when the alkali is contained in the molded catalyst elements.

The reaction rate is very high, and it is easily possible to produce from 100 to 300 parts by weight of tertiary amine I per liter of catalyst per hour.

The catalysts usually retain their activity and selectivity in the process of the invention over long periods (eg 2 to 3 years).

The substituents $R^1$, $R^2$, and $R^3$ in the compounds I and II and in the alcohol $R^3$—OH have the following meanings:

$R^1$, $R^2$, and $R^3$ independently denote:

$C_1$–$C_{12}$ alkyl, such as methyl, ethyl, n-propyl, isopropyl, n-butyl, isobutyl, sec-butyl, tert-butyl, n-pentyl, isopentyl, sec-pentyl, neopentyl, 1,2 -dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, and isododecyl and preferably $C_1$–$C_8$ alkyl, such as methyl, ethyl, n-propyl, isopropyl, n-butyl, isobutyl, sec-butyl, tert-butyl, n-pentyl, isopentyl, sec-pentyl, neopentyl, 1,2-dirnethylpropyl, n-hexyl, isohexyl, sec-hexyl, n-heptyl, isoheptyl, n-octyl, and isooctyl and more preferably $C_1$–$C_4$alkyl, such as methyl, ethyl, n-propyl, isopropyl, n-butyl, isobutyl, sec-butyl, and tert-butyl.

Examples of particularly suitable alcohols $R^3$—OH are monohydric aliphatic alcohols $R^3$—OH, eg, ethanol, n-propanol, isopropanol, n-butanol or sec-butanol, hexanol, and decanol.

Suitable secondary amines II are, eg, dimethylamine, methylethylamine, diethylamine, diisopropylamine, di-n-butylamine, and ethyl-n-hexylamine.

Tertiary amines I which can be classified as dimethyl fatty alkylamines in which the fatty alkyl radical generally has a carbon number exceeding 8 are of special commercial interest for the manufacture of quaternary ammonium compounds such as phase transfer catalyst soft rinsing agents (*cf* Römps Chemielexikon, 8th Edition, 1987, Vol. 5, pp. 3438 to 3439).

Low molecular weight tertiary amines I are used industrially in large quantities, for example as catalysts for the manufacture of polyurethanes or epoxy resins.

EXAMPLES

In the following examples the parts are by weight and relate to parts by volume as do kilograms to liters.

Example 1

For the continuous preparation of ethyldimethylamine use was made of liquefied dimethylamine of commercial quality and ethanol azeotrope denatured with 1.2% of toluene (95.6% of ethanol, 4.4% of water).

The amination was carried out in a vertical reaction tube having a reaction mixture capacity of 1000 parts by volume. The ratio of the diameter to the length of the reaction tube was 1:40. By means of an organic heat transfer medium, which was subjected to pump circulation in a heating jacket, it was possible to effect thermostatic control of the reaction tube. The reaction tube was packed with 700 parts by volume of catalyst G22 (Südchemie AG) having the form of cylinders measuring 3 mm in height and 3 mm in diameter. The catalyst was reduced, ie, activated, and protected from loss of activity by submergence under decanol.

If the catalyst is used in non-preactivated form, it can be activated and reduced with hydrogen in the following manner: approximately 300 parts by volume per hour of ethanol are allowed to trickle over the catalyst, through which a nitrogen/hydrogen mixture is passed upwardly followed by pure hydrogen at a temperature of from 180° to 200° C. The activation of the catalyst reaches completion when no more additional water of reduction from the catalyst is detectable in the ethanol azeotrope.

To cause the reaction to take place, 100 parts by volume of dimethylamine and 300 parts by volume of ethanol were then fed per hour upwardly through the furnace at a temperature of 200° C. and an overall pressure of 50 bar (hydrogen partial pressure ca 10 bar). Roughly 0.1 part by volume of hydrogen as off-gas was passed to the head of the receiver per hour. The reaction product leaving the receiver had the following composition as determined by gas-chromatographic analysis and analysis by destillation (calculated free from water):

trimethylamine: <0.1 wt % methylethylamine: <0.1 wt % dimethylamine: 0.2 wt % dimethylethylamine: 60.0 wt % diethylmethylamine: <0.1 wt % ethanol: 38.0 wt % toluene: 1.5 wt %

Dimethylethylamine having a purity better than 99.8 % can be obtained from the crude mixture by distillation.

Example 2

Example 1 was repeated except that a mixture of 8 parts of diethylamine and 1 part of ethanol was alkylated. The overall pressure (partial pressure of the reaction mixture plus the partial pressure of the hydrogen) was 50 bar and the reaction temperature was 210° C. 1000 parts by volume of the mixture of diethylamine and ethanol were passed through 700 parts by volume of catalyst per hour. There was produced a reaction product having the following composition (calculated free from water) as determine by gas chromatography:

unknown substances: <0.1% by area monoethylamine: <0.1% by area diethylamine: 48.9% by area triethylamine: 49.6% by area ethanol: 0.2% by area

I claim:
1. A process for the preparation of a trialkylamine of the formula

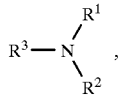 (I)

in which $R^1$, $R^2$, and $R^3$ denote $C_1$–$C_{12}$ alkyl,
by the reaction of a dialkylamine of the formula II

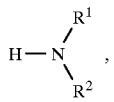 (II)

in which $R^1$ and $R^2$ denote $C_1$–$C_{12}$ alkyl,
with alcohols $R^3$—OH in the presence of a (copper chromite/alkaline-earth metal chromite)-containing hydrogenation/dehydrogenation catalyst, wherein the reaction is carried out in the liquid phase over a fixed bed catalyst in the presence of the water formed during the reaction at temperatures ranging from 180° to 210° C. and pressures ranging from 40 to 120 bar.

2. A process for the preparation of a trialkylamine I as defined in claim 1, wherein the reaction is carried out in the presence of hydrogen.

3. A process for the preparation of a trialkylamine I as defined in claim 1, wherein the reaction is carried out under a hydrogen partial pressure of from 10 to 50 bar.

4. A process for the preparation of a trialkylamine I as defined in claim 1, wherein the reaction is carried out in the presence of from 0.001 to 2 wt % of an alkali metal oxide, an alkaline-earth metal oxide, an alkali metal oxide, and/or an alkaline-earth metal oxide.

* * * * *